(12) United States Patent
O'Connell

(10) Patent No.: US 6,478,767 B1
(45) Date of Patent: Nov. 12, 2002

(54) DIALYSIS PROBE

(76) Inventor: Mark Thomas O'Connell, 23 Gordon Close, Little Paxton, St. Neots, Huntingdon PE19 4PF (GB)

( * ) Notice: Subject to any disclaimer, the term of this patent is extended or adjusted under 35 U.S.C. 154(b) by 0 days.

(21) Appl. No.: 09/762,856

(22) PCT Filed: Aug. 18, 1999

(86) PCT No.: PCT/GB99/02747

§ 371 (c)(1),
(2), (4) Date: Apr. 12, 2001

(87) PCT Pub. No.: WO00/10464

PCT Pub. Date: Mar. 2, 2000

(30) Foreign Application Priority Data

Aug. 18, 1998 (GB) ............................................. 9817877

(51) Int. Cl.⁷ ................................................. A61M 1/00
(52) U.S. Cl. .......................... 604/27; 604/264; 604/174
(58) Field of Search ............................. 604/27, 28, 29, 604/264, 174; 210/321.6, 321.72, 321.78, 321.87

(56) References Cited

U.S. PATENT DOCUMENTS 5,191,900 A * 3/1993 Mishra ........................ 422/947
5,554,148 A * 9/1996 Aebischer et al. .......... 604/265
5,607,390 A * 3/1997 Patsalos et al. ............. 604/174

* cited by examiner

*Primary Examiner*—Brian L. Casler
*Assistant Examiner*—Mark Han
(74) *Attorney, Agent, or Firm*—Elman & Associates; Gerry J. Elman

(57) ABSTRACT

A dialysis probe comprises a mechanically-strong membrane carrier, or support, which is an elongate, rod-like, support member having at its distal end an eye, or a notch, and a relatively-flexible, open-ended, semipermeable membrane. The opposed sides of the support member are shaped to accommodate the membrane when it is folded in a U-fashion through the eye or notch and lies against each of the opposed sides of the support member between its distal and proximal ends.

16 Claims, 3 Drawing Sheets

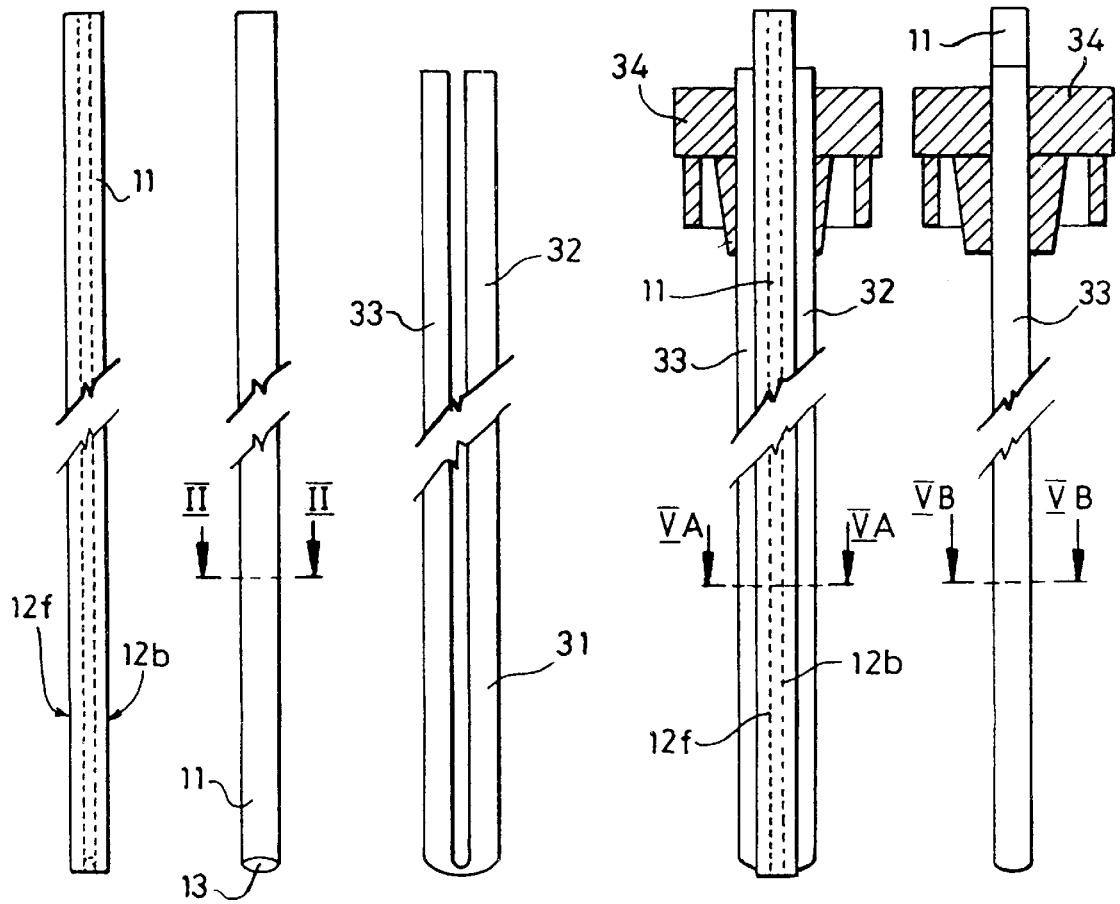
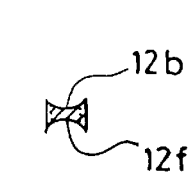
Fig. 2
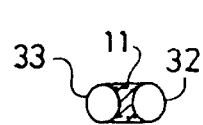
Fig. 5A
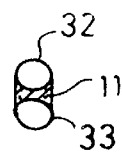
Fig. 5B

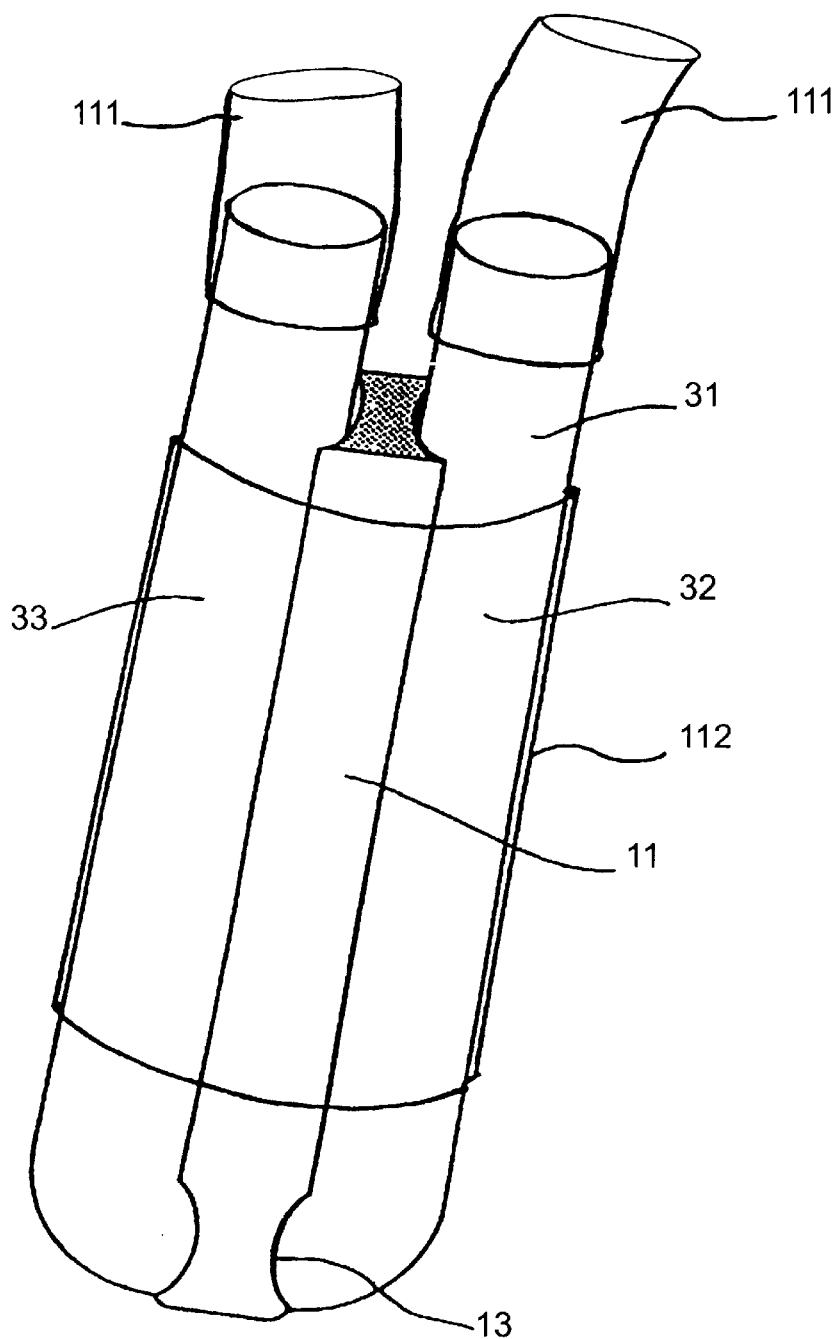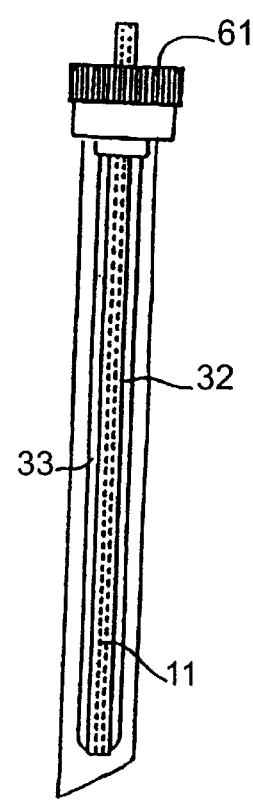
Fig. 11
Fig. 12

DIALYSIS PROBE

FIELD OF THE INVENTION

This invention is concerned with dialysis probes, and relates in particular to a novel form of carrier for use as part of such a probe, and to a probe when using such a carrier.

BACKGROUND OF THE INVENTION

Dialysis is the process of separating a liquid that is a solution in some solvent of one or more dissolved substance, or solute, mixed with one or more colloid (a material which is insoluble in the solvent and yet is present as particles which are so small that they behave in some ways as though they were in fact dissolved). In this process the mixture is placed in contact with a semipermeable membrane—a solid barrier that acts as an extremely fine sieve—through which the smaller solute particles can pass (diffuse) from one side to the other while the much larger colloidal particles cannot, and this diffusion/passage is then allowed/encouraged to take place. It is usual to have more solvent—the perfusion fluid—running past on the other side of the membrane, so that the solute particles are washed away as they emerge. Such a dialysis system can be used to separate off and retain either of the two types of component. Thus, it may be that the colloidal material kept on the one side of the membrane is wanted, and the solute passing through to the other side of the membrane is not, or vice versa.

A well-known use of dialysis in the modern world is in the artificial kidney, or "dialysis machine", where the mixture to be separated is the blood of a person with damaged or failed kidneys. This blood contains not only the desirable red blood cells as a colloidal solution but also an excess of potentially harmful dissolved materials that should normally have been removed by the Patient's kidneys. In the dialysis treatment the Patient's blood is continuously drawn out through a needle inserted into a vein (usually in the arm), and fed to the dialysis machine where the harmful constituents are separated off using a semipermeable membrane, as described above, and then returned, cleansed and "purified", into the Patient.

Another common, but not so well-known, use of dialysis is in the taking for subsequent chemical and biological analysis of tiny samples of body fluid/tissue components in human or veterinary medicine (in certain branches of modern Research Medicine much attention is being given to using this technique to assist in a determination of brain functions). Sampling is normally effected by inserting into the body a very fine, hollow probe containing a suitable membrane contactable with the body fluid or tissue, and pumping perfusion liquid therethrough to fetch out the diffused solute therein—the material of interest. The body fluid to be sampled is usually, but not always, blood, and in such a case it is normal to insert the dialysis probe directly into an artery or vein, and allow the dialysis to occur in situ.

Dialysis probes can take a number of different physical forms. An earlier type of probe was essentially a sleeve-like tube a few millimeters in diameter and made of some impermeable material with one end—its distal (or "far") end, to be inserted into the body—closed by a suitable semipermeable membrane, and with smaller tubes sealingly inserted into the other end—the proximal (or "near") end, by which the tube was handled—to allow perfusion fluid to be supplied to—fed to and withdrawn from the interior (the lumen) of—the sleeve. In use the distal end of such a probe is inserted into a suitable body tissue or cavity—some part of the brain, say, or a vein or artery—and perfusion fluid is pumped in, through and out of the sleeve, taking with it any materials that have diffused from the body through the distal-end membrane into the sleeve's lumen.

A more recent design of probe is essentially a sleeve-like tube itself made of semipermeable material—and so forming the membrane—blocked off at the distal end and with perfusion fluid supply tubes sealingly inserted into the proximal end. In use the membrane sleeve is inserted into the body, often through a previously-emplaced protective cannula (a slightly larger-diameter and mechanically-stronger sleeve, or sheath, positioned in the body to lead into the area of interest), and perfusion fluid is pumped in, through and out, taking with it any materials that have diffused from the body contents through the membrane walls of the sleeve into the lumen thereof.

Although all these forms of dialysis probe can provide excellent results, nevertheless they suffer from a number of significant drawbacks. For example, the membrane, which is extremely fragile, can too easily be damaged by the internalization—the emplacement therewithin—of the perfusion liquid supply tubes. Moreover, fluid outflow (leakage) can too easily occur, so lessening the effectiveness of the device, due to the generation of back-pressure caused by the reduction of tubing diameter between the lumen of the membrane and the lumen of the internalized outlet tubing. In addition, such probes are difficult to insert into tissue because of the lack of rigidity of the body of the probe (the rigidity that exists is due solely to the internalized tubing, and this is often insufficient to prevent concertinaing or folding of the membrane when the device is inserted into tissue).

The present invention suggests a solution to - or at least a mitigation of—these problems, thus providing a dialysis probe that can be readily and safely inserted into tissue as well as being relatively easy to manufacture, by a simple but surprising novel design of probe that incorporates a new sort of membrane carrier, or support. More specifically, the invention suggests the use of a mechanically-strong membrane carrier, or support, which is an elongate, rod-like, support member having at its distal end an eye, or a notch, through which a relatively-flexible, open-ended, tubular semipermeable membrane can be passed (rather like a strand of cotton is threaded through the eye of a needle), and wherein most preferably the opposed sides of the support member are shaped so as at least partially to accommodate the tubular membrane when the latter is folded back (at the eye/notch), U-fashion, and caused to lie against and either side of the support member between its distal and proximal ends. In use the tubular-membrane-carrying support member is inserted into the target area of the body, preferably through a previously-emplaced protective cannula, and perfusion fluid is pumped directly through the tubular membrane from one end to the other, taking with it any materials that have diffused from the body contents through the membrane walls into its lumen. It will be appreciated that the support member provides the probe with all the required mechanical strength, and that its simplified construction renders much easier its manufacture.

SUMMARY OF THE INVENTION

The present invention provides a dialysis probe comprising a membrane carrier; a relatively flexible, open-ended, semipermeable membrane; and inlet and outlet tubes, wherein the membrane carrier is a stiff, elongate support member having two opposed sides and a proximal end and a distal end, the distal end having at least one eye or one notch through which the membrane passes and is folded, U-fashion, whereby the membrane lies along the two opposed sides of the support member and whereby the ends of the membrane are adjacent the proximal end of the support member; and wherein the inlet and outlet tubes are sealingly joined to the two ends of the membrane, whereby perfusion liquid may be passed through the membrane.

The opposed sides of the support member may be shaped so as to accommodate at least partially the tubular membrane when the latter is so folded back and caused to lie against the support member. The invention provides a membrane carrier for use as part of a dialysis probe. In general, therefore, the carrier will be of dimensions and materials that are suitable for this use, and more is said about this hereinafter.

DESCRIPTION OF THE DRAWINGS

FIGS. 1A/B show respectively side and front views of a membrane carrier of the invention (without the membrane tubing fitted);

FIG. 2 shows a section taken along the line II—II in FIG. 1;

FIG. 3 shows a side view of the membrane tubing in the configuration that would be assumed when it is fitted to the carrier of FIG. 1A;

FIGS. 4A/B show respectively side and front views of the membrane carrier of

FIGS. 1A/B and the membrane tubing of FIG. 3 when fitted together and having an anchoring member in the form of a cannula cap (shown cut-away);

FIGS. 5A/B are sections taken along the lines VA—VA and VB—VB in FIG. 4;

FIG. 11 is a perspective view of the probe of FIG. 4 (but with inlet/outlet tubes and sleeve-like sheath and without the cap); and FIG. 12 shows a side view of the probe of FIGS. 4A and 6 fitted with a cannula cap anchoring member.

DETAILED DESCRIPTION

Figure 6:
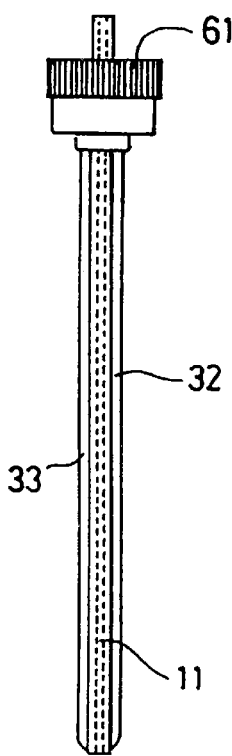
FIG. 6 shows a side view of the probe of FIG. 4A fitted with a cannula cap anchoring member.

With particular reference to FIGS. 1 and 3, the membrane carrier of the invention is a stiff, elongate, rod-like, support member. The support member is stiff—that is to say, it provides significant resistance to forces acting to bend and fold it and it is this factor which provides the membrane carrier with the required mechanical strength. However, the support member is not rigid, and can preferably bend, or flex, a limited amount so that when it is in a particularly long form it can be inserted into the body a considerable distance from the target area, and can follow the twists and turns taken by the body as it is pushed in to its destination. A typical case of this is when the probe is inserted into a vein in the leg, and is pushed along until it reaches the Patient's heart. It is not easy to quantify the stiffness that permits such flexibility yet also provides acceptable resistance to folding, except by reference to the specific materials mentioned hereinafter from which the member can advantageously be made, and to the dimensions of the member (even intrinsically-rigid materials such as glass become surprisingly flexible when in the form of a long, very thin, element).

Basically, the support member is an elongate, but thin, rod. The rod's length depends primarily upon where the probe is to be used, and what its target area is—for the leg-vein-to-heart route just mentioned the probe might be around 30 in (75 cm) long, while for simple insertion into an artery it might be no more than 3 in (7.5 cm) long. The rod's width is small—for use as part of a probe that may be from as little as 0.5 to as much as 5 mm in width the support member may itself be from around 0.2 to 4 mm width—to ensure it can pass through the body (and especially along small veins and arteries) without causing significant damage to the surrounding tissues. Most preferably, though, the probe is somewhat smaller—from 0.05 to 0.5 mm—so that the support member is smaller still—from around 0.02 to 0.2 mm. Naturally, the smaller the width, and within reason the greater the length, the more flexible the probe will be.

The support member has at its distal end (the end to be inserted into the body) an eye, or a notch. A notch is conveniently formed as a shallow recess at the very tip—the actual end—of the support member, while an eye may be positioned anywhere near the end. Obviously, the eye's or notch's dimensions will be such as to accommodate the tubular membrane.

There may be more than one eye/notch, enabling the support member to carry more than one tubular membrane. More particularly, there may at the tip of the member be two eyes—or one eye and one notch—arranged to be orthogonal one to the other and slightly spaced apart along the length of the member. In this way the member can carry two tubular membranes, one disposed such as to be lying against, say, the "front" and "back" surfaces of the member and the other disposed to be lying against the two "side" surfaces of the member. By making the two membranes of different materials, or by in some other way giving them different semipermeability, and perhaps also by using different perfusion fluids, so a single probe can be constructed that can be used to sample two different materials at once.

In use, the dimensions of the support member—and more specifically the location of the notch or eye at its distal end—enable there to be maintained the correct length of membrane in relation to the tissue surrounding it, while its stiffness prevents folding of the fragile membrane upon insertion.

As noted above, the support member is made of a material which is suitable for a probe, and which—bearing the probe's dimensions in mind—allows the member to be both stiff and yet also flexible. Such materials are mainly resilient plastics such as polycarbonate, polypropylene and polyvinyl chloride, but other possible materials are stainless steel, titanium and glass.

Figure 10:
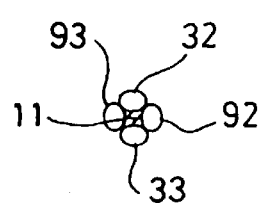
FIG. 10 is a section taken along the line X—X in FIG. 9.

Most preferably the opposed sides of the invention's support member are so shaped that each provides a shallow recess, extending the length of the support member, in which there can at least partially be accommodated in use the tubular membrane when the latter is so folded back, U-fashion, and caused to lie against and either side of the support member. See FIGS. 2, 5A, 5B and 10. Conveniently each recess has an arcuate cross section more or less matching the external diameter of the tubular membrane, and is of a depth roughly equivalent to the radius of the membrane. Thus, when the membrane is in place it nestles in the recess in contact with the support member, and so is both protected and supported by the member. Where the support member carries two orthogonally-arranged tubular membranes then both the side and the front/back surfaces of the member are suitably recessed, and the member then has an X-like cross-section. See FIG. 10.

The distal end of the support member may be sharpened or blunted, depending on how the probe of which it is a part is intended to be used. Thus, it can be sharpened/pointed to allow the probe to penetrate body tissue to reach the site of interest (as might be the case when investigating brain chemistry), while it may on the contrary be blunted/rounded to reduce the probe's ability to penetrate body tissue (as would be preferred when threading the probe along a vein or artery). See FIGS. 8A and 8B.

The proximal end of the support member may conveniently carry some form of handle and/or fastening means by which the probe of which it is a part can be manipulated and/or attached to the Patient, and these means may be integral with or themselves attached (by glue, for instance) to the member. In the simplest case the fastening means may be little more than a thin laterally-oriented plate extending either side of the member rather like a pair of wings, which in use—with the probe inserted into the body—can be taped or sutured to the body surface either side of the insertion point. See FIGS. 4A & 4B. However, most preferably use of the probe is associated with use of a matching cannula, and the cannula is fastened to the Patient while the probe is then fastened to the cannula. In this case lateral wings can also be used, clipping on to matching wings on the cannula itself, while an alternative is to provide the support member with a distal-end screw-top, cap, plug or stopper, which fits to and is secured to a matching socket at the distal end of the cannula.

One convenient form of plate-like anchoring member has its wings so flexible that they can be bent together for gripping between the finger and thumb to facilitate the insertion of the probe into tissue. The plate-like member is preferably formed from two parts, one part overlying the other, and the dialysis membrane, carrier member (and when present, the sheath: see hereinafter) may be located between the two parts. Such an arrangement can allow moulding of the dialysis membrane, carrier member and sheath, together with the plate-like member, to given an extremely secure bond.

With particular reference to FIG. 6, one convenient form for a stopper or cap type of securing or anchoring member comprises a central plug portion (to enter into the interior of the cannula), an annular head portion extending transversely to the axis of the probe, and an annular wall projected from the annular head portion towards the distal end of the probe to engage the exterior of the cannula. The interior of the annular wall may be provided with a screw thread (for use with a cannula arranged to receive such a screw-threaded cap). This form of stopper is made of resilient plastic material, and by such means a secure seal in the lumen of the cannula can readily be obtained.

With particular reference to FIG. 4A, the invention is a dialysis probe which is a combination of a support member and a tubular semipermeable membrane. Thus, the support member has a relatively-flexible, open-ended, tubular semipermeable membrane passed through the member's eye/notch, and folded back, U-fashion, to lie against and either side of the support member between its distal and proximal ends. The membrane may be constructed of any suitable material, bearing in mind the nature of the body fluids to be sampled. It may selectively allow substances to transverse it on any appropriate basis—on the basis of their molecular weight (in effect, their size) or instead (or also) on the basis of ligand binding affinity, for example. Typical such membrane materials are cellulose, cellulose-acetate, polyamide, polycarbonate-ether, polyethersulphone, polyimide and polyvinylidine difluoride, and suitable membranes made therefrom are available under the names CUPROPHAN and VITAFIBER from Enka AG, Hospal Ltd and Spectrum Inc. The membranes in such tubular semipermeable membranes are about 0.01 mm thick, and the tubes are around 0.21 to 2.50 mm external diameter (and so 0.20 to 2.49 mm internal diameter), and although delicate can with care successfully be folded double, U-fashion, about the eye/notch of the support member to lie back against the member (and within its recess, if it has one).

A probe of the invention utilizes a semipermeable membrane that is in the form of a continuous tube extending from the probe's proximal end to—and "around"—the distal end and then back up to the proximal end, and in use a suitable perfusion fluid is pumped into, through and then out of this tube, taking with it any diffused solute material. The perfusion fluid is fed to and withdrawn from the tubular membrane through inlet and outlet tubes—matching fine plastic tubes glued to/into the membrane—though conveniently the membrane itself extends beyond any attachment means it may be employing, and may even extend beyond the actual proximal end of the support member, so facilitating coupling of the membrane to the relevant accessory tubing for connection to external apparatus to enable the delivery of perfusate or the collection of dialysate.

With particular reference to FIGS. 4A, 4B, 6 and 11, in such a use the probe may be placed within the body via a cannula, which assists both in locating the probe within the correct area and also in shielding and protecting the probe. And by so shielding the membrane the cannula can also ensure that it is only in the area of interest that the probe—the tip of the probe, say, and thus the membrane at that part—is exposed to the body fluid from which a sample of material is desired. See FIG. 11 Such an arrangement prevents dialysis from occurring near the proximal end of the probe. This shielding effect can also be achieved by providing the probe with an impermeable sheath (that perhaps extends from the proximal end down toward the distal end). Such a sheath may either be a separate component, that covers the relevant portion of the probe like a sleeve, or it may be some form of coating produced on and effectively integral with the appropriate lengths of the membrane (the use of a coating or sleeve bonded to the anchoring member is a relatively safe way of providing a sheath that is not in danger of breaking off into the body of the subject).

The cannula or sheath may, for example, extend to within 20 centimeters, within 2 centimeters, or within 0.2 centimeters of the distal end of the dialysis membrane.

As will be apparent from what has been said above, the invention provides a dialysis probe that can be readily and safely inserted into tissue as well as being relatively easy to manufacture. The probe's preferred embodiments may be summarized as follows:—

The probe consists of a stiffened membrane carrier that supports one or more looped dialysis membrane each of which is in the form of a tubular semi-permeable membrane which is open at both ends to enable perfusion fluid to pass from one end of the tube to the other. The membrane carrier—the probe's supporting member has one or more notch or 'eye' at its distal end (which end may be either blunt or sharp, as appropriate to the probe's intended use), and it is through each notch/eye that the relevant tubular membrane passes to form a U-loop configuration. The supporting member, and more specifically the location of the notches/eyes thereon, maintains the correct length of membrane in relation to the tissue surrounding it, and prevents folding of the fragile membrane upon insertion.

A sheath extends from the proximal end of the probe and terminates part-way towards the distal end, so as to limit the area of dialysis membrane over which dialysis can take place. See FIG. 11

Figure 7:
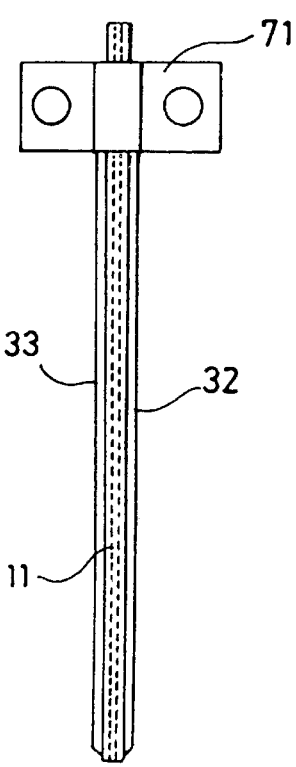
FIG. 7 shows a side view of the probe of FIG. 4A but with a flattened plate-like anchoring member.

With particular reference to FIGS. 6 & 7, an anchoring member is positioned at the proximal end of the probe to provide a releasable attachment for securing it to the outside of the body of the subject, and each of the tubular membrane, membrane carrier and (when present) the sheath is bonded to the anchoring member. The attachment means is arranged to be secured releasable and indirectly to the body of the subject, and is typically a stopper surrounding the dialysis membrane for plugging the lumen of a cannula secured to the outside of the subject. Such an arrangement enables the probe to be used with a cannula left in situ for an extended period of time and also usable for other purposes, such as the introduction of therapeutic agents or diagnostic agents. Alternatively, the anchoring member is a flattened plate-like member whose plane is substantially parallel to the axis of the membrane carrier, which member comprises wing extensions on opposite sides of the longitudinal axis of the membrane carrier. See FIG. 7.

Such a probe can be readily manufactured, and is particularly safe for use in the body of the subject since the anchoring member, the bonding of components to it, and the securing of the probe to the outside the body of the subject all taken together greatly reduce the risk that any part of the probe will break free and be lost in the body of the subject.

An embodiment of the invention is now described, though by way of illustration only:

The carrier/support member of FIG. 1—seen from the side in FIG. 1A and from the front in FIG. 1B—is a length of resiliently-stiff plastic rod (11) with its two front and back (as viewed) faces (12f, 12b) concavely arcuate along its entire length (see the section of FIG. 2), and with a small laterally-extending eye (13) at the very tip of its distal end (the bottom end as viewed). The semipermeable membrane (31) of FIG. 3 is flexible enough to be threaded through the eye 13—see FIGS. 4/5—and then bent double into a U-shape with each arm (32,33) lying against the side of the carrier 11 and accommodated within the recess in the relevant face 12.

FIGS. 4A,B show side and front views of a probe made by assembling the support member 11 and tubular membrane 31 of FIGS. 1 and 3, and fitting the combination with a cap (34: this is shown in section). FIG. 6 shows a side view of the probe of FIG. 4A fitted with a cannula cap anchoring member (61), while for comparison FIG. 7 shows a side view of the probe of FIG. 4A but with a flattened plate-like anchoring member (71).

Figures 8A, 8B:
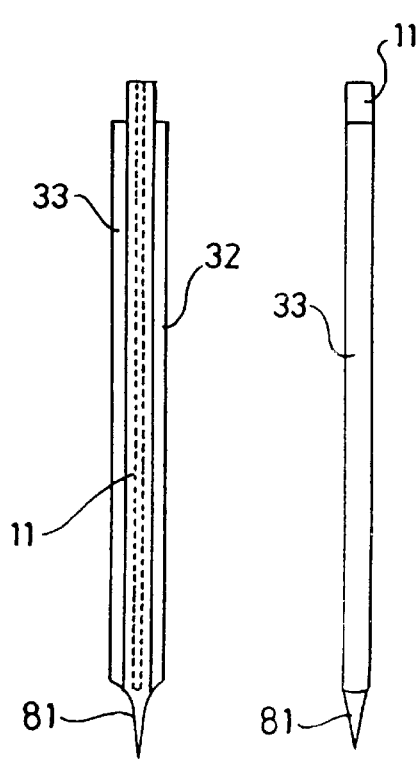
FIGS. 8A/B show respectively side and front views of a probe like that of FIG. 4A but with a sharpened distal end to the membrane support member.

FIGS. 8A/B show respectively side and front views of a probe like that of FIG. 4A but with a sharpened distal end (81) to the membrane support member 11 (the eye 13 through which the membrane 31 passes is not separately shown, but it is in this embodiment somewhat inboard of the very end of the support member 11).

Figures 9A, 9B:
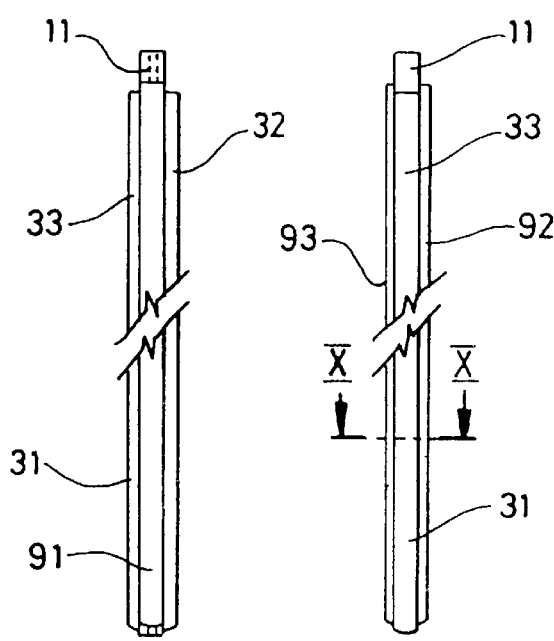
FIGS. 9A/B show respectively side and front view of a probe with two membrane tubes mounted on a single membrane carrier.

FIGS. 9A/B show respectively side and front view of a probe with two membrane tubes (31 and 91) mounted on a single membrane carrier 11 with the plane of the U of one normal to the plane of the U of the other. The tubes 91,92 pass a notch at the bottom of rod 11. As can be seen from the section of FIG. 10, the support member is "X"-shaped to allow both membranes to be accommodated thereby. As is the case with membrane tube 31 described above, membrane tube 91 is folded into a U-shape with each arm 91, 93 lying against the side of the carrier 11.

FIG. 11 shows the probe membrane tube 31 and support 11 of FIG. 4, but with the addition of the necessary inlet/outlet tubes (111) and the shielding sleevelike sheath (112) (shown as though they were transparent, so that the underlying structure can also be seen).

What is claimed is:

1. A dialysis probe comprising:
   a membrane carrier;
   a flexible, open-ended, tubular semipermeable membrane; and
   inlet and outlet tubes,
      wherein the membrane carrier is a stiff, elongate support member having two opposed sides and a proximal end and a distal end, the distal end having at least one eye or one notch through which the membrane passes and is folded, U-fashion, whereby the membrane lies along the two opposed sides of the support member and whereby the ends of the membrane are adjacent the proximal end of the support member; and
      wherein the inlet and outlet tubes are sealingly joined to the two ends of the membrane, whereby perfusion liquid may be passed through the membrane.

2. The probe of claim 1, wherein the support member provides flexibility for accommodating the contours of bodily tissue during its transport and positioning at the location of its use in the body.

3. The probe of claim 1, wherein the support member is from 0.02 to 0.2 mm in width.

4. The probe of claim 1, wherein the distal end of the support member has two eyes, or one eye and one notch, which are arranged orthogonally relative to each other and spaced apart along the length of the support member.

5. The probe of claim 4, wherein the support member comprises a recess extending the length of each of the opposed sides, which recess is adapted to accommodate the membrane to lie along the length of each of the opposed sides when the membrane is folded back, U-fashion.

6. The probe of claim 5, wherein each recess has an arcuate cross section that is similar in size to the external diameter of the membrane and in depth to the radius of the membrane.

7. The probe of claim 1, wherein there is more than one eye or notch, enabling the support member to carry more than one membrane.

8. The probe of claim 1, wherein the proximal end of the support member comprises a fastening means by which the probe may be manipulated or attached to the body.

9. The probe of claim 8, wherein the fastening means is a handle.

10. The probe of claim 8, wherein the fastening means is a laterally-oriented plate extending the opposed sides of the support member, whereby the plate, when the probe is inserted into the body, may be taped or sutured to the body.

11. The probe of claim 10, further comprising a cannula having a lateral plate, whereby the laterally-oriented plate of the probe may be fastened to the lateral plate of the cannula during use.

12. The probe of claim 11, wherein the support member further comprises a screw-top, cap, plug or stopper, which fits to and is secured to a matching socket at the proximal end of the cannula.

13. The probe of claim 1, wherein the inlet and outlet tubes are affixed to accessory tubing, connected to the membrane, which carries perfusion fluid to or from the membrane.

14. The probe of claim 13, wherein the membrane extends beyond the proximal end of the support member, thereby facilitating coupling of the membrane to accessory tubing for connection to external apparatus to enable the delivery of perfusate or the collection of dialysate.

15. The probe of claim 1, further comprising an impermeable sheath surrounding the membrane and extending a distance from the proximal end of the membrane toward its distal end, whereby the sheath limits the surface area of the membrane over which dialysis may take place.

16. The probe of claim 15 wherein the sheath is a coating produced on and is effectively integral with a portion of the membrane.

* * * * *